(12) United States Patent
Lee et al.

(10) Patent No.: US 9,563,320 B2
(45) Date of Patent: Feb. 7, 2017

(54) FLEXIBLE DISPLAY APPARATUS

(71) Applicant: SAMSUNG ELECTRONICS CO., LTD., Suwon-si (KR)

(72) Inventors: Ga-eun Lee, Suwon-si (KR); Yong-jun Lim, Seoul (KR); Kyung-wan Park, Suwon-si (KR); Shi-yun Cho, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/706,450

(22) Filed: May 7, 2015

(65) Prior Publication Data

US 2016/0062503 A1    Mar. 3, 2016

(30) Foreign Application Priority Data

Aug. 28, 2014  (KR) .................. 10-2014-0113346

(51) Int. Cl.
| | |
|---|---|
| G06F 3/045 | (2006.01) |
| G06F 3/044 | (2006.01) |
| G06F 1/16 | (2006.01) |
| G01N 3/20 | (2006.01) |
| G06F 3/041 | (2006.01) |
| G01L 1/22 | (2006.01) |

(52) U.S. Cl.
CPC ............ *G06F 3/044* (2013.01); *G01L 1/2206* (2013.01); *G01N 3/20* (2013.01); *G06F 1/16* (2013.01); *G06F 3/0412* (2013.01); *G06F 2203/04102* (2013.01); *G06F 2203/04103* (2013.01)

(58) Field of Classification Search
CPC ......... G06F 3/044; G06F 3/045; G06F 3/0412
USPC .................. 345/173–179; 178/18.01–18.04
See application file for complete search history.

(56) References Cited

U.S. PATENT DOCUMENTS

| | | | |
|---|---|---|---|
| 8,072,437 B2 | 12/2011 | Miller et al. | |
| 2010/0045705 A1* | 2/2010 | Vertegaal | A47G 19/2227 345/661 |
| 2012/0242592 A1* | 9/2012 | Rothkopf | G06F 1/1652 345/173 |
| 2012/0256720 A1 | 10/2012 | Byun et al. | |
| 2014/0008999 A1* | 1/2014 | Prest | G01L 1/22 307/119 |
| 2014/0204285 A1* | 7/2014 | Jang | G06F 3/044 349/12 |
| 2014/0347287 A1* | 11/2014 | Lee | G06F 1/1652 345/173 |

FOREIGN PATENT DOCUMENTS

| | | |
|---|---|---|
| KR | 10-2012-0114961 A | 10/2012 |
| KR | 10-1239255 B1 | 3/2013 |

OTHER PUBLICATIONS

Purcher, "Samsung Invents Flex-Displays that will warn Consumers that they're Over-Bending their Devices", Patent Bolt, May 28, 2013, 5 pages.

* cited by examiner

*Primary Examiner* — Kimnhung Nguyen
(74) *Attorney, Agent, or Firm* — Sughrue Mion, PLLC

(57) ABSTRACT

Provided is a flexible display apparatus. A shape deformation sensor is formed in at least one of a first plurality of connection lines of a flexible display panel and a second plurality of connection lines of a touch screen panel. The shape deformation sensor is configured to sense a shape deformation of the flexible display panel.

15 Claims, 14 Drawing Sheets

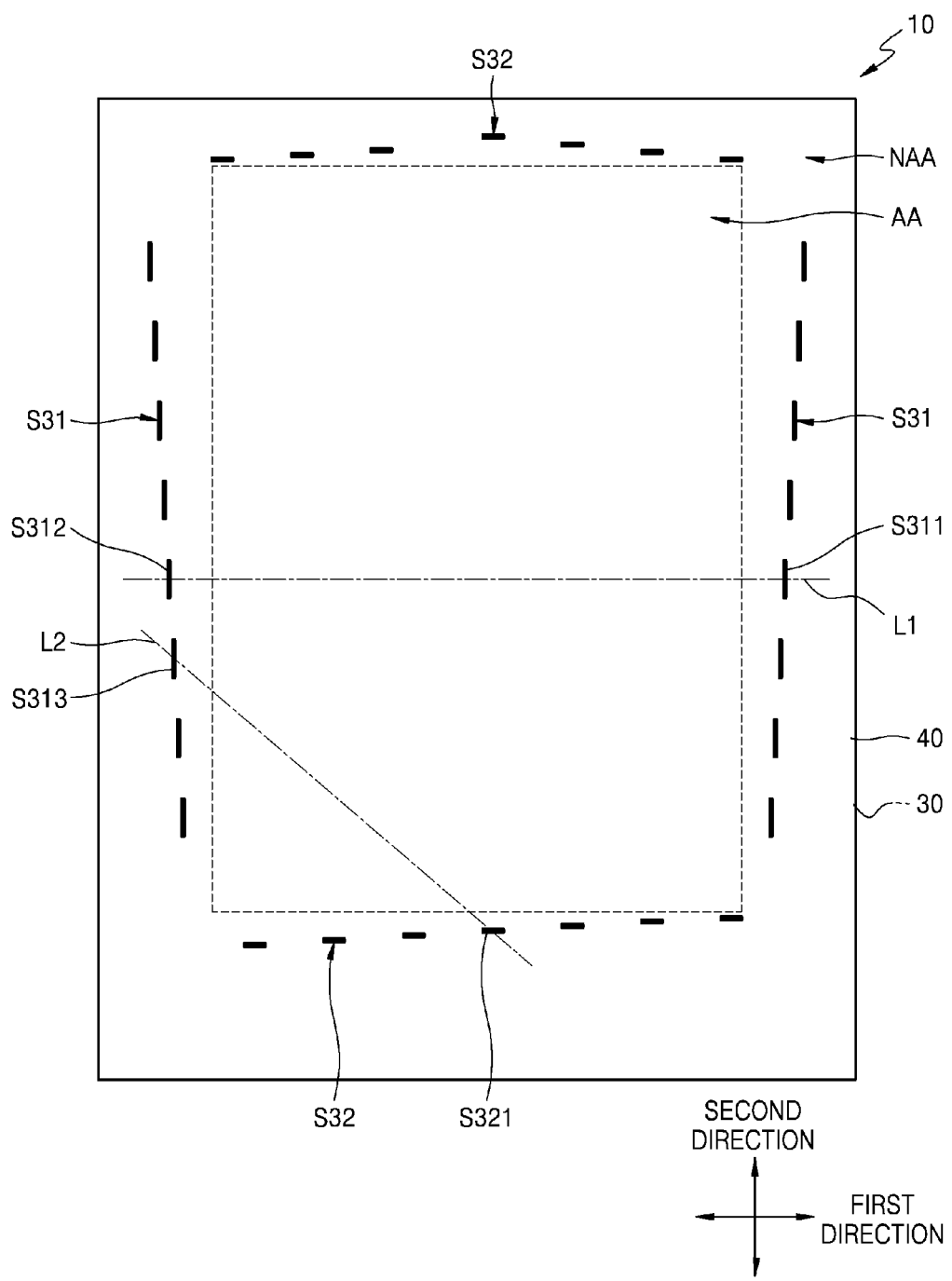

FLEXIBLE DISPLAY APPARATUS

RELATED APPLICATION

This application claims priority from Korean Patent Application No. 10-2014-0113346, filed on Aug. 28, 2014, in the Korean Intellectual Property Office, the disclosure of which is incorporated herein by reference in its entirety.

BACKGROUND

1. Field

One or more exemplary embodiments relate to a flexible display apparatus.

2. Description of the Related Art

In recent years, with the advent of an information-oriented society, display apparatuses configured to process a large amount of information and display the information have progressed quickly. Thus, various display apparatuses have been developed and highlighted.

A liquid crystal display (LCD) device, a plasma display panel (PDP) device, a field emission display (FED) device, and an electroluminescence display (ELD) device have been developed as display apparatuses. These display apparatuses are gradually being made to be relatively thin and light-weight and to consume low power. However, since the above-mentioned display apparatuses use a glass substrate to resist high heat generated during a fabrication process, there may be a technical limit to making the display apparatuses thin and lightweight or flexible.

Accordingly, much attention has recently been paid to development of a flexible display apparatus capable of retaining display performance even if the flexible display apparatus is bent like paper, by using a flexible material (e.g., a plastic film) which is capable of being folded and unfolded, instead of an inflexible glass substrate. The flexible display apparatus may be thin and lightweight, highly resistant to impact, and carried while being folded or rolled because the flexible display apparatus may be warped or bent. Further, the flexible display apparatus may be manufactured in any of various shapes and thus, widely applicable in the future.

The above-described flexible display apparatus may adopt a sensor configured to sense a shape deformation in order to measure an extent to which the flexible display apparatus is folded or bent and a direction in which the flexible display apparatus is folded or bent. As an example of a sensor configured to sense a deformation of a shape of the flexible display apparatus, a transparent electrode material applicable to touch screens or a hall sensor may be used.

A structure using the transparent electrode material may include a plurality of horizontal electrodes and a plurality of vertical electrodes that are arranged to intersect one another. The structure using the transparent electrode material may be utilized in a variety of ways, not only in display devices but also in the field of touch screens. In a shape deformation sensing technique using the transparent electrode material, since an additional ITO film is adhered to a top surface or bottom surface of a flexible display panel, a thickness of the flexible display apparatus may be bound to increase. When the thickness of the flexible display apparatus increases, a radius of curvature that may be allowed during a folding or bending operation may be limited. In particular, as the thickness of the flexible display apparatus increases, a displacement of an inner surface or outer surface may increase during the folding or bending operation, and the flexible display apparatus may be more likely be damaged.

Further, since an indium tin oxide (ITO) film applied to a typical touch screen may detect a state of contact or non-contact with respect to a specific point, the ITO film may be technically limited when it comes to detecting simultaneous deformation (i.e., folding or bending operations) of several points or detecting a bending extent and direction.

In a structure using a hall sensor configured to sense a magnetic field, a plurality of hall sensors may be arranged in a widthwise or lengthwise direction of a flexible display apparatus, and a variation in the position of a magnetic body disposed at a specific point may be detected in order to sense a deformation of the flexible display apparatus. However, a shape deformation sensing structure using a hall sensor may be limited in that deformation may be sensed under specific conditions, for example, in that a deformation of the flexible display apparatus (e.g., carrying the flexible display apparatus while being rolled or folded) may be sensed only when the deformation occurs only in a direction in which hall sensors are arranged. Furthermore, it may be difficult for the structure using the hall sensor to sense a folding or bending extent and direction.

SUMMARY

One or more exemplary embodiments include a flexible display apparatus, which may precisely sense various types of deformation of the flexible display apparatus and prevent an increase in the thickness of the flexible display apparatus.

Additional aspects will be set forth in part in the description which follows and, in part, will be apparent from the description, or may be learned by practice of the presented exemplary embodiments.

According to one or more exemplary embodiments, a flexible display apparatus includes a flexible display panel which includes a display area in which a plurality of pixels are disposed, and a non-display area formed outside of the display area and in which a first plurality of connection lines connected to the pixels are disposed, wherein at least a portion of the flexible display panel is capable of being bent, and a touch screen panel which includes an active area in which sensing electrodes are disposed, and a non-active area formed outside of the active area and in which a second plurality of connection lines connected to the sensing electrodes are disposed. A shape deformation sensor is formed in at least one of the first plurality of connection lines of the flexible display panel and the second plurality of connection lines of the touch screen panel, wherein the shape deformation sensor is configured to sense a shape deformation of the flexible display panel The shape deformation sensor may include a strain gauge of which an electrical resistance varies based on a sensed amount of the shape deformation.

The shape deformation sensor may include a same material as the at least one of the first plurality of connection lines of the flexible display panel and the second plurality of connection lines of the touch screen panel in which the shape deformation sensor is formed.

The shape deformation sensor may extend from the at least one of the first plurality of connection lines of the flexible display panel and the second plurality of connection lines of the touch screen panel in which the shape deformation sensor is formed.

The sensing electrodes of the touch screen panel may include first sensing electrodes formed in a first direction and second sensing electrodes formed in a second direction that intersects the first direction. The first plurality of connection lines of the touch screen panel may include first connection lines connected to both end portions of the first sensing electrodes in the first direction, and second connection lines connected to both end portions of the second sensing electrodes in the second direction.

At least two sections of the first connection lines may extend in the second direction. A respective component of the shape deformation sensor may be formed in each of the at least two sections of the first connection lines that extend in the second direction.

The respective components of the shape deformation sensor formed in the first connection lines may be disposed apart from one another in the second direction.

At least two sections of the second connection lines may extend in the first direction. Respective components of the shape deformation sensor may be formed in each of the at least two sections of the second connection lines that extend in the first direction.

The respective components of the shape deformation sensor formed in the second connection lines may be disposed apart from one another in the first direction.

BRIEF DESCRIPTION OF THE DRAWINGS

These and/or other aspects will become apparent and more readily appreciated from the following description of exemplary embodiments, taken in conjunction with the accompanying drawings in which:

FIG. 5 is a plan view of the flexible display apparatus shown in FIG. 1A;

DETAILED DESCRIPTION

Figure 1A:
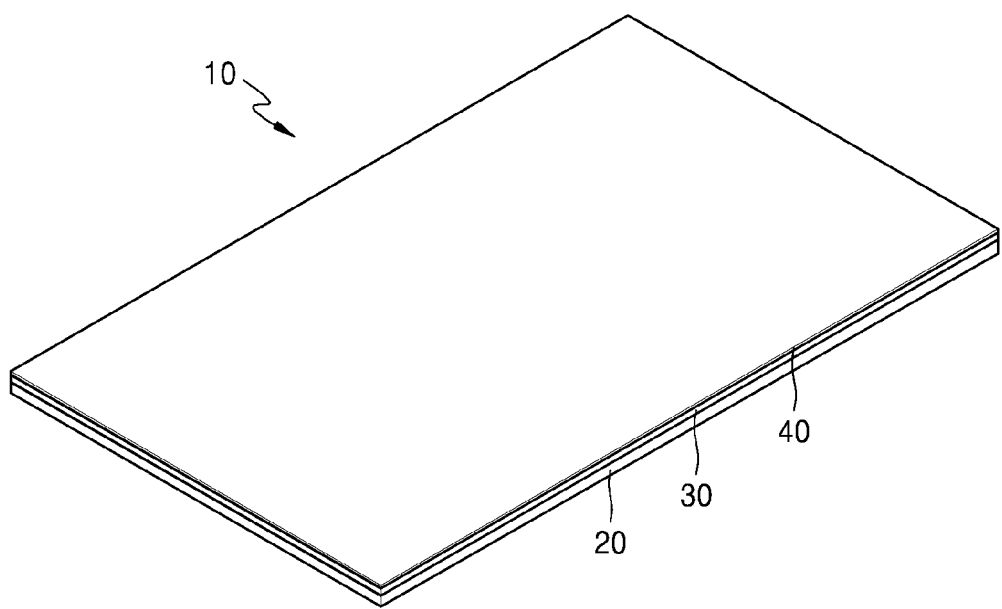
FIGS. 1A and 1B are respectively an assembled perspective view and exploded perspective view of a flexible display apparatus, according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

A flexible display apparatus according to exemplary embodiments will now be described in detail with reference to the accompanying drawings, in which the exemplary embodiments are shown. In the drawings, the same reference numerals or symbols denote components or elements that perform substantially the same functions.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present inventive concept. As used herein, the term "and/or" includes any and all combinations of one or more of the associated listed items.

The terminology used herein is for the purpose of describing particular embodiments only and is not intended to be limiting of the present inventive concept. As used herein, the singular forms "a", "an", and "the" are intended to include the plural forms as well, unless the context clearly indicates otherwise. It will be further understood that the terms "comprises", "comprising", "includes", and/or "including" when used herein, specify the presence of stated features, integers, steps, operations, elements, and/or components, but do not preclude the presence or addition of one or more other features, integers, steps, operations, elements, components, and/or groups thereof.

Figure 1B:
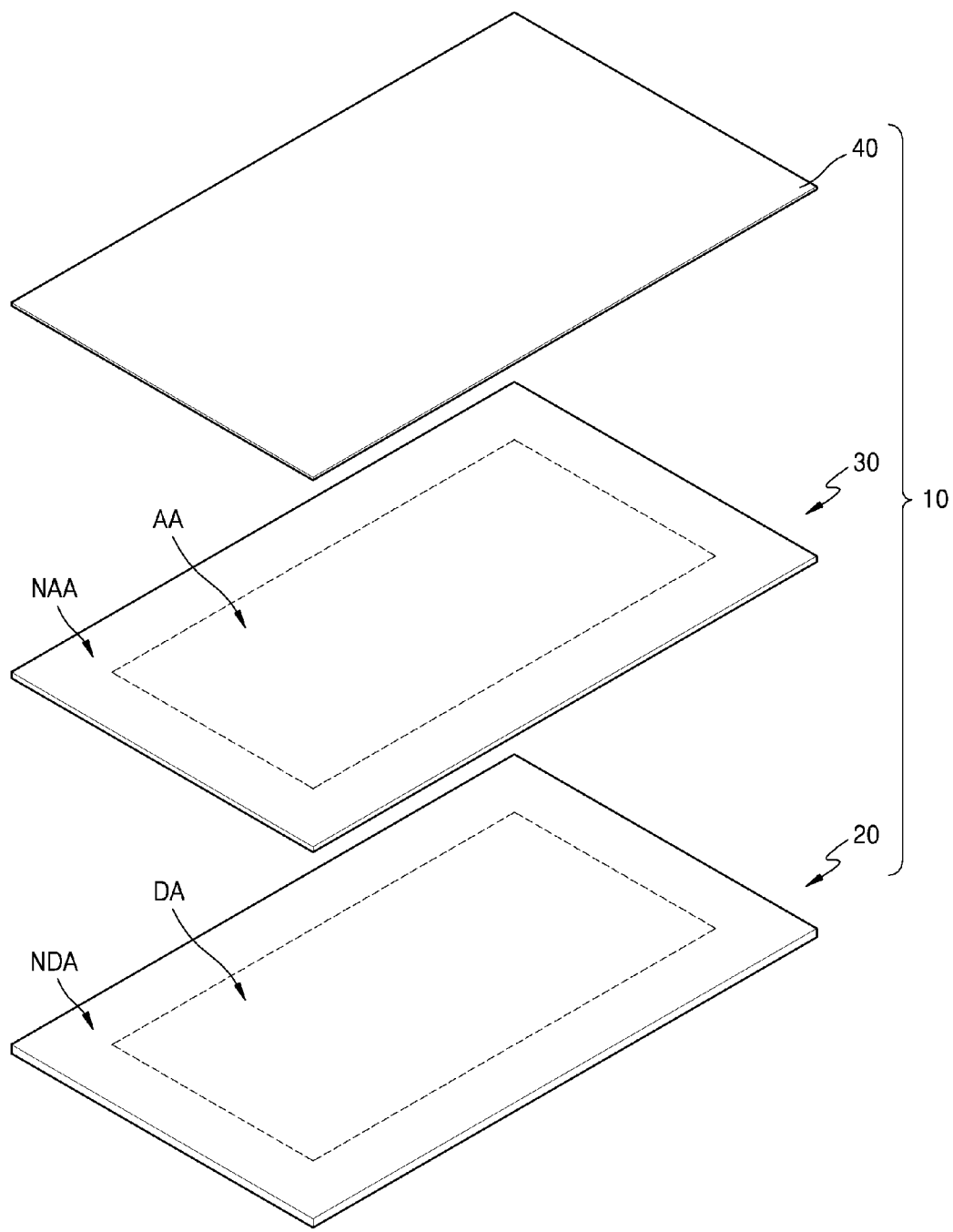
Figure 2:
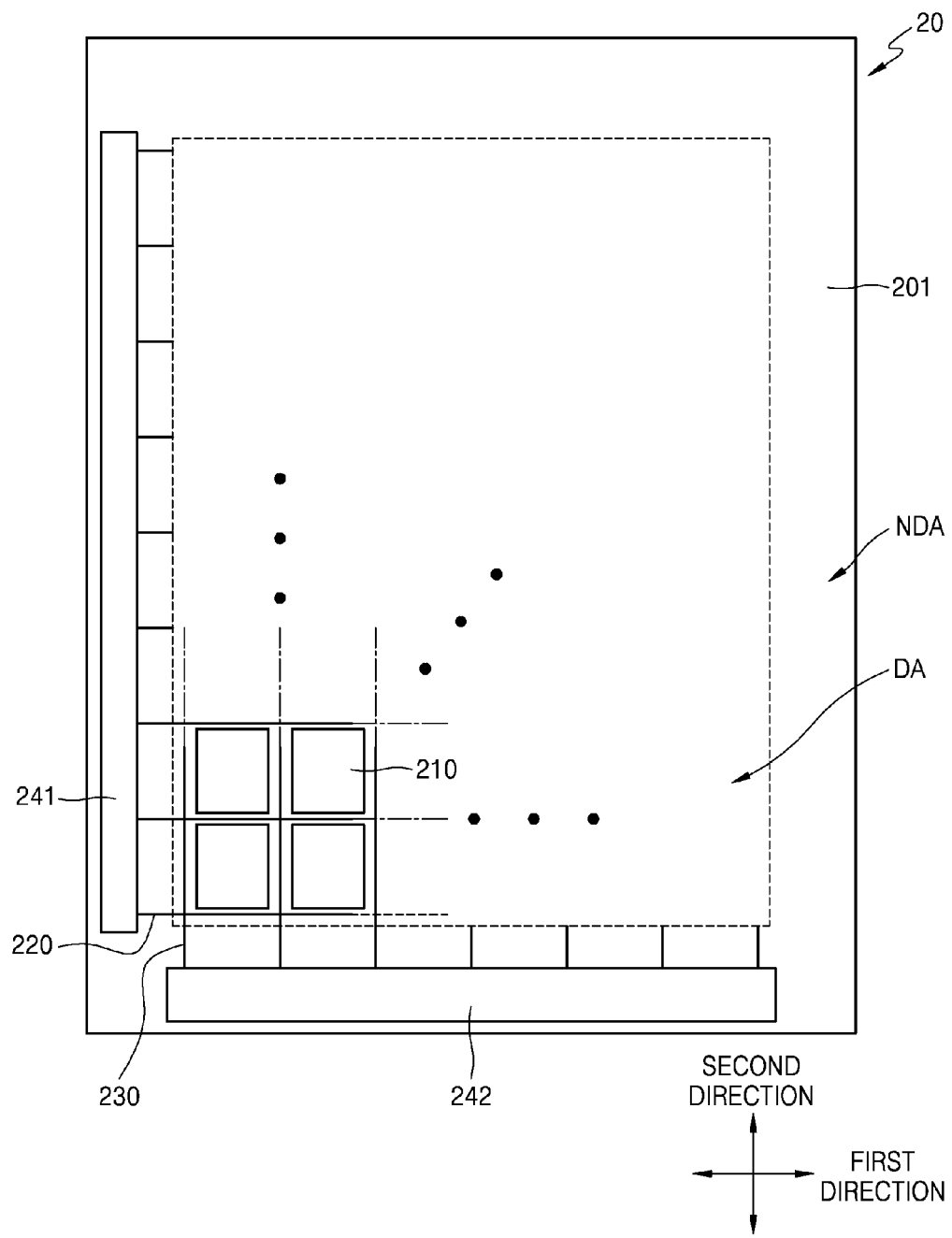
FIG. 2 is a plan view of a flexible display panel of FIG. 1A, according to an exemplary embodiment.
Figure 3:
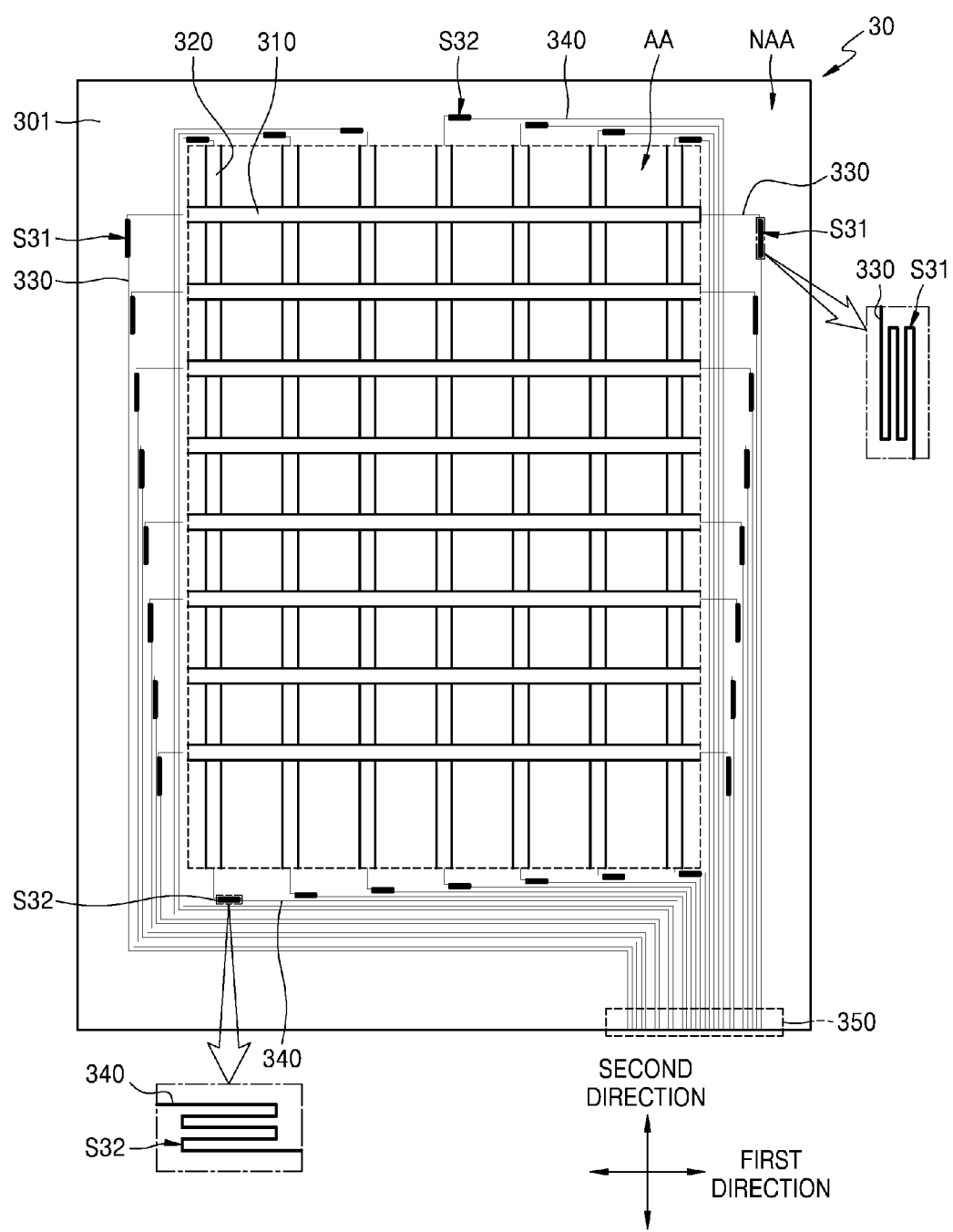
FIG. 3 is a plan view of a touch screen panel of FIG. 1A, according to an exemplary embodiment.

FIGS. 1A and 1B are respectively an assembled perspective view and exploded perspective view of a flexible display apparatus 10, according to an exemplary embodiment. FIG. 2 is a plan view of a flexible display panel 20 of FIG. 1A, according to an exemplary embodiment. FIG. 3 is a plan view of a touch screen panel 30 of FIG. 1A, according to an exemplary embodiment.

Referring to FIGS. 1A and 1B, the flexible display apparatus 10 may include a flexible display panel 20, a touch screen panel 30, and a window 40.

The flexible display panel 20 may be configured to display an image, and at least a portion of the flexible display panel 20 may be bendable. The flexible display panel 20 may include a display area DA, which is configured to display images on a screen, and a non-display area NDA, which is formed outside of the display area DA.

As shown in FIG. 2, the flexible display panel 20 may include a substrate 201, a plurality of pixels 210 disposed on the substrate 201, and connection lines 220 and 230 connected to the pixels 210. The connection lines 220 and 230 may be respectively connected to a gate driver 241 and a data driver 242.

The substrate 201 of the flexible display panel 20 may have characteristics which relate to flexibility. The substrate 201 may be a plastic substrate. For example, the substrate 201 may include any one selected from among polyethersulfone (PES), polyacrylate (PAR), polyetherimide (PEI), polyethylene naphthalate (PEN), polyethylene terephthalate (PET), polyphenylene sulfide (PPS), polyallylate, polyimide (PI), polycarbonate (PC), poly(arylene ether sulfone), and a combination of two or more thereof.

The plurality of pixels 210 may be disposed in the display area DA, and at least some of the connection lines 220 and 230 may be disposed in the non-display area NDA. The gate driver 241 may be disposed in the non-display area NDA.

Although not shown, each of the pixels 210 may include a display device, two thin-film transistors (TFTs), and a capacitor. The display device may include, but is not limited thereto, an organic light-emitting diode (OLED) and/or a liquid crystal (LCD) device. Further, the number of TFTs and the number of capacitors are exemplarily described above, and each of the pixels 210 may include three or more TFTs and/or two or more capacitors.

The connection lines 220 and 230 of the flexible display panel 20 may electrically connect the pixels 210 with the gate driver 241 and may also electrically connect the pixels 210 with the data driver 242. The connection lines 220 and 230 may have electrical conductivity. As an example, the connection lines 220 and 230 may include metal lines. For example, the metal lines may be formed of copper (Cu), aluminum (Al), or silver (Ag).

The connection lines 220 and 230 may include gate lines and data lines (hereinafter, the connection lines 220 and 230 are respectively referred to as the gate lines 220 and the data lines 230). The gate lines 220 may extend in a first direction, and the data lines 230 may extend in a second direction. The gate lines 220 may be connected to the gate driver 241 and may be configured to receive a scan signal from the gate driver 241. The data lines 230 may be connected to the data driver 242 and may be configured to receive a data signal from the data driver 242. Although not shown, the data lines 230 may include a driving power line and may be configured to externally receive driving power.

The touch screen panel 30 may be configured to receive a touch input from a user, and may be disposed on the flexible display panel 20 as shown in FIG. 1B. The touch screen panel 30 may include an active area AA configured to receive the touch input and a non-active area NAA formed outside of the active area AA. The active area AA may overlap the display area DA. The active area AA may completely or partially overlap the display area DA.

As shown in FIG. 3, the touch screen panel 30 may include a substrate 301 and sensing electrodes 310 and 320 and connection lines 330 and 340 disposed on the substrate 301. A pad unit (also referred to herein as a "pad device") 350 may be connected to end portions of the connection lines 330 and 340.

The substrate 301 of the touch screen panel 30 may have characteristics which relate to flexibility. The substrate 301 may be a plastic substrate. For example, the substrate 301 may include any one selected from among PES, PAR, PEI, PEN, PET, PPS, polyallylate, PI, PC, poly(arylene ether sulfone), and a combination of any two or more thereof.

The sensing electrodes 310 and 320 may be configured to receive a touch input from a user and may be disposed in the active area AA of the touch screen panel 30. The sensing electrodes 310 and 320 may include a transparent electrode. The transparent electrode may include at least one from among an indium tin oxide (ITO) electrode, a carbon nanotube (CNT) electrode, a graphene electrode, a silver nanowire electrode, and a metal mesh electrode.

The sensing electrodes 310 and 320 may include first sensing electrodes, which may extend along a first direction, and second sensing electrodes, which may extend in a second direction that is at an angle with respect to (or intersects) the first direction (hereinafter, the sensing electrodes 310 and 320 are respectively referred to as first sensing electrodes 310 and second sensing electrodes 320). The first direction may be at a right angle with respect to the second direction. The first sensing electrodes 310 may be disposed apart from one another in the second direction, and the second sensing electrodes 320 may be disposed apart from one another in the first direction.

Each of the first sensing electrodes 310 and the second sensing electrodes 320 may have a straight shape (i.e., an elongated rectangular shape). However, the above-described example of the first sensing electrodes 310 and the second sensing electrodes 320 may be only an example, and the first sensing electrodes 310 and the second sensing electrodes 320 may be embodied in any of various shapes. For example, each of the first and second sensing electrodes 310 and 320 may include a plurality of sub-electrodes having lozenge shapes and/or hexagonal shapes connected in first and second directions.

The connection lines 330 and 340 may be configured to transmit electric signals input via the first and second sensing electrodes 310 and 320 to the pad unit 350 and may be disposed in the non-active area NAA. The connection lines 330 and 340 may have electrical conductivity. As an example, the connection lines 330 and 340 may include metal lines. For example, the metal lines may be formed of copper, aluminum, or silver. However, the connection lines 330 and 340 are not limited to the above-described materials, and may include the same material as the first and second sensing electrodes 310 and 320.

The connection lines 330 and 340 may include first connection lines connected to the first sensing electrodes 310, and second connection lines connected to the second sensing electrodes 320 (hereinafter, the connection lines 330 and 340 are respectively referred to as first connection lines 330 and second sensing electrodes 340).

The first connection lines 330 may be connected to both end portions of the first sensing electrodes 310 in the first direction. The first connection lines 330 may electrically connect the first sensing electrodes 310 with the pad unit 350, respectively.

The second connection lines 340 may be connected to both end portions of the second sensing electrodes 320 in the second direction. The second connection lines 340 may electrically connect the second sensing electrodes 320 with the pad unit 350, respectively.

At least some sections of the first connection lines 330 may extend in the second direction. The first connection lines 330 may be arranged apart from one another in the first direction. At least some sections of the second connection lines 340 may extend in the first direction. The second connection lines 340 may be arranged apart from one another in the second direction.

As shown in FIG. 1B, the window 40 may be disposed on the touch screen panel 30. The window 40 may include a transparent material. The window 40 may protect the touch screen panel 30 and the flexible display panel 20, while an image displayed on the flexible display panel 20 may be transmitted through the window 40 and exposed.

The above-described exemplary embodiment of the flexible display apparatus 10 is an example in which the touch screen panel 30 is disposed as an additional layer on the flexible display panel 20. However a structure of the flexible display apparatus 10 is not limited thereto. For example, the touch screen panel 30 may be disposed under the flexible display panel 20 or formed inside the flexible display panel 20.

Figure 4A:
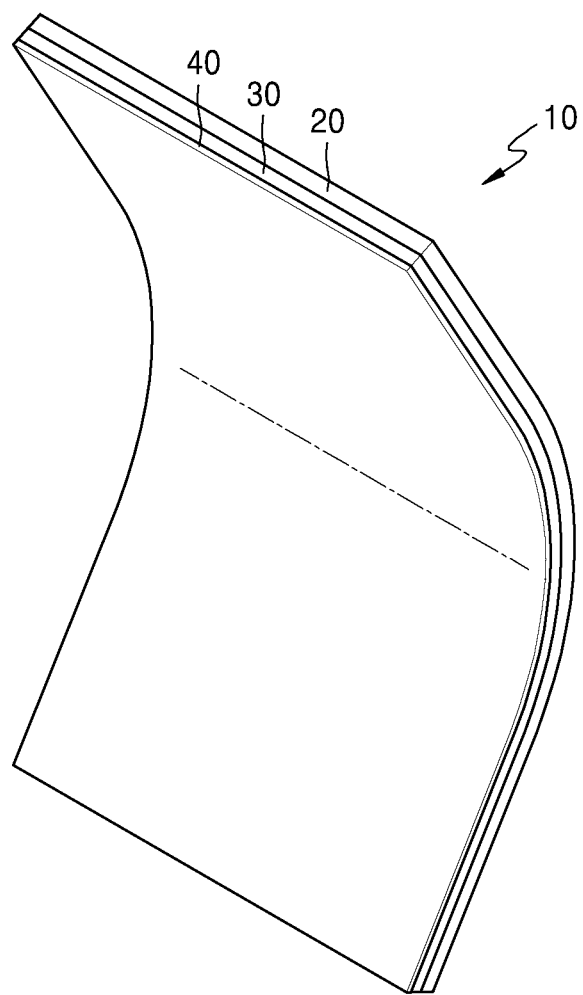
FIGS. 4A, 4B, 4C, and 4D are schematic diagrams of examples in which a shape of the flexible display apparatus shown in FIG. 1A is deformed.
Figure 4B:
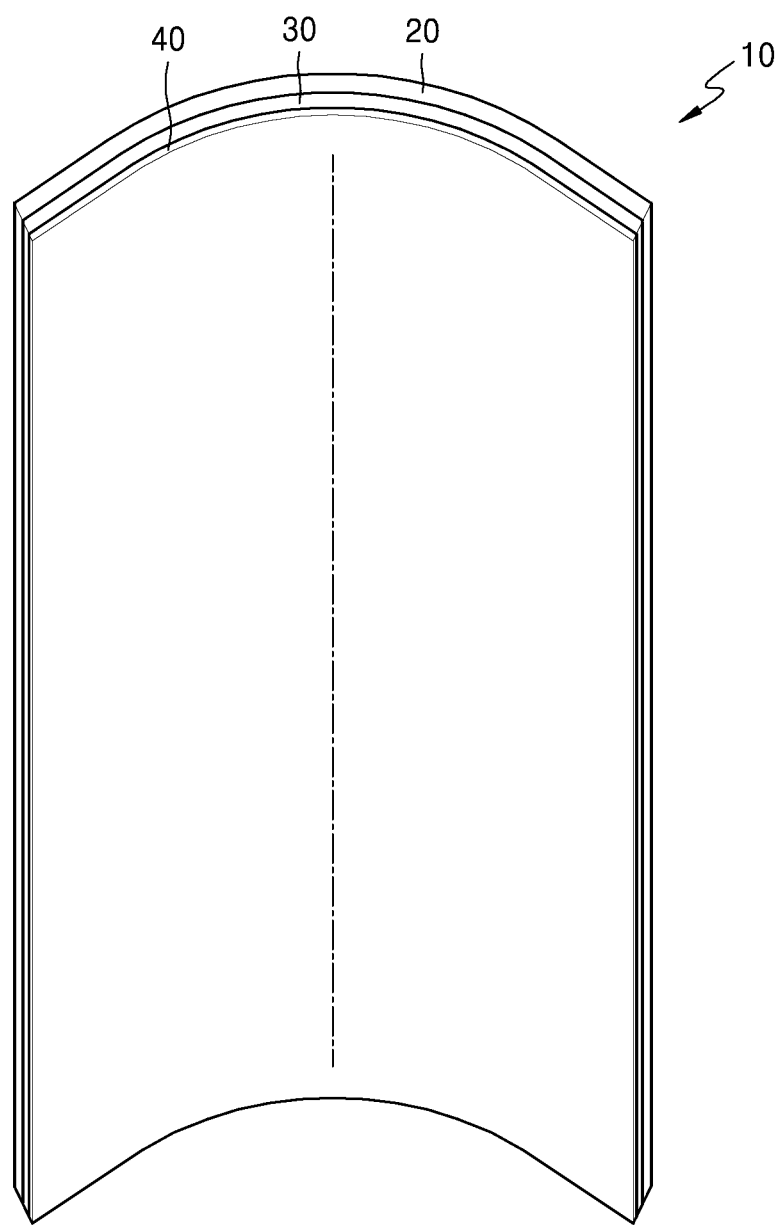
Figure 4C:
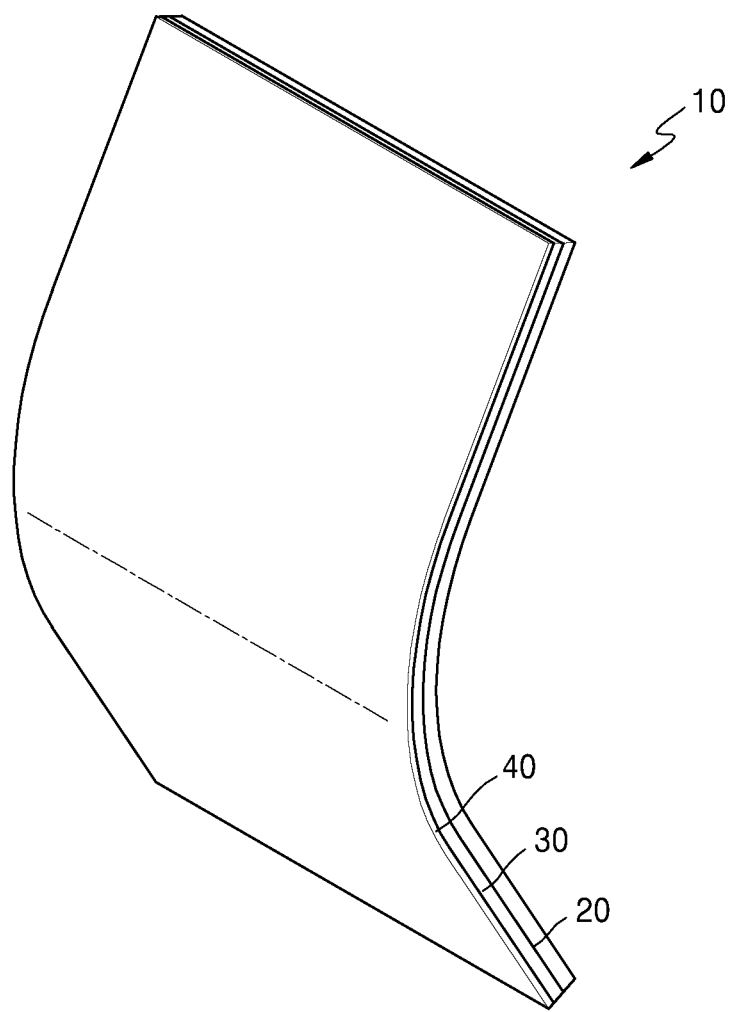
Figure 4D:
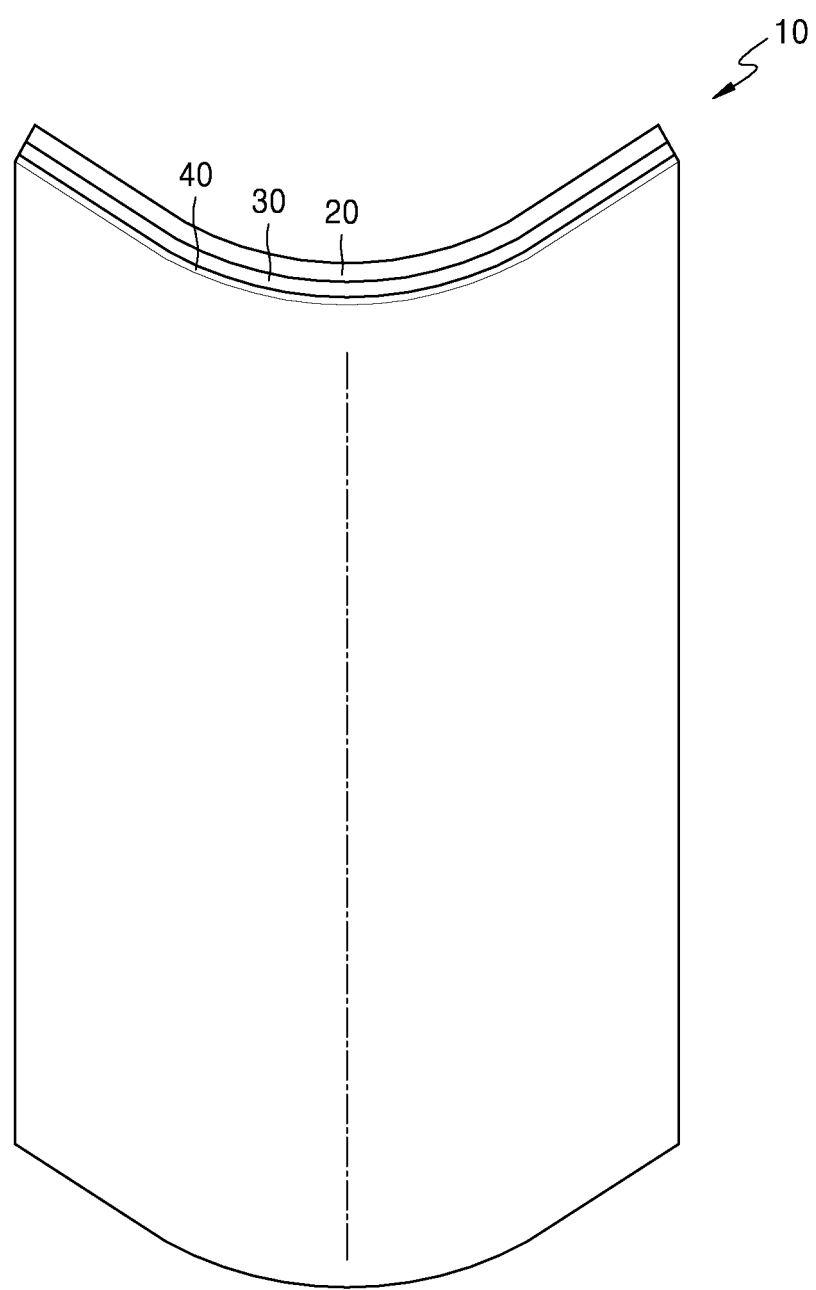

The flexible display apparatus 10 according to an exemplary embodiment may be foldable and/or bendable. For example, the flexible display apparatus 10 may be bendable such that the window 40 becomes convex, as shown in FIGS. 4A and 4B, or such that the window 40 becomes concave, as shown in FIGS. 4C and 4D. In addition, although not shown, the flexible display apparatus 10 may have a partially bent corner or may be completely wound or bent, as, for example, a roll type.

The flexible display apparatus 10 that may be bendable may include shape deformation sensing units (also referred to herein as "shape deformation sensors") S31, S32, S21, and S22 configured to sense an extent to which the flexible display apparatus 10 is folded or bent, i.e., an amount of deformation, and a direction in which the flexible display apparatus 10 is folded or bent.

In the flexible display apparatus 10 according to the present exemplary embodiment, the shape deformation sensing units S31, S32, S21, and S22 may be respectively formed in the first, second, gate, and data connection lines 330, 340, 220, and 230 used in the touch screen panel 30 or the flexible display panel 20. In the present exemplary embodiment, since shapes of the first, second, gate, and data connection lines 330, 340, 220, and 230 may be partially deformed to form the shape deformation sensing units S31, S32, S21, and S22, an additional layer for a sensor configured to sense shape deformation may not be added to the flexible display apparatus 10. Thus, an increase in the thickness of the flexible display apparatus 10 may be prevented.

For example, referring back to FIG. 3, the shape deformation sensing units S31 and S32 may be respectively formed in the first and second connection lines 330 and 340 of the touch screen panel 30.

The shape deformation sensing units S31 and S32 may be formed in at least one of first connection lines 330 and second connection lines 340 of the touch screen panel 30.

Each of the shape deformation sensing units S31 and S32 may include a strain gauge of which an electrical resistance varies according to the amount of shape deformation of the shape deformation sensing units S31 and S32. In particular, the electrical resistance of each of the shape deformation sensing units S31 and S32 may vary in proportion to the amount of strain applied during the shape deformation. For example, when the shape deformation sensing units S31 and S32 are being bent, lengths of electrical lines constituting the shape deformation sensing units S31 and S32 may increase, while sectional areas of the electrical lines may be reduced, thereby increasing electrical resistances of the shape deformation sensing units S31 and S32. By measuring the increased electrical resistances of the shape deformation sensing units S31 and S32, the bending of the flexible display apparatus 10 may be sensed and measured.

The shape deformation sensing units S31 may be formed by partially deforming patterns of the first connection lines 330. For example, the shape deformation sensing units S31 may extend from the first connection lines 330. Each of the first connection lines 330 may include an extension section that extends in the second direction. A repetitive pattern that reciprocates forward and backward in the second direction may be formed in the extension section of each of the shape deformation sensing units S31.

The shape deformation sensing unit S31 may include the same material as the first connection line 330. As an example, the shape deformation sensing unit S31 may include a copper wire. As another example, the shape deformation sensing unit S31 may include any one or more of an ITO film, a silver nanowire, and/or a metal mesh.

The shape deformation sensing units S31 formed in the first connection lines 330 may be disposed apart from one another in the second direction. Since the first sensing electrodes 310 are disposed apart from one another in the second direction, the first connection lines 330 connected to the first sensing electrodes 310 may have different lengths in the second direction. Thus, since the first connection lines 330 have different lengths in the second direction, it may be relatively easy to separately form the shape deformation sensing units S31 apart from one another in the second direction.

In addition, at least some of the first connection lines 330 may be disposed apart from one another in the first direction. Thus, at least some of the shape deformation sensing units S31 formed in the first connection lines 330, respectively, may be located at different positions, not only in the second direction but also in the first direction.

The shape deformation sensing units S32 may be formed by partially deforming patterns of the second connection lines 340. For example, the shape deformation sensing units S32 may extend from the second connection lines 340. Each of the second connection lines 340 may include an extension section that extends in the first direction. A repetitive pattern that reciprocates forward and backward in the first direction may be formed in the extension section of each of the shape deformation sensing unit S32.

The shape deformation sensing unit S32 may include the same material as the second connection line 340. As an example, the shape deformation sensing unit S32 may include a copper wire. As another example, the shape deformation sensing unit S32 may include any of an ITO film, a silver nanowire, and/or a metal mesh.

The shape deformation sensing units S32 formed in the second connection lines 340 may be disposed apart from one another in the first direction. Since the second sensing electrodes 320 are disposed apart from one another in the first direction, the second connection lines 340 connected to the second sensing electrodes 320 may have different lengths in the first direction. Thus, since the second connection lines 340 have different lengths in the first direction, it may be relatively easy to separately form the shape deformation sensing units S32 apart from one another in the first direction.

At least some sections of the second connection lines 340 may be disposed apart from one another in the second direction. Thus, at least some of the shape deformation sensing units S32 formed in the second connection lines 340, respectively, may be located at different positions, not only in the first direction but also in the second direction.

FIG. 5 is a plan view of the flexible display apparatus 10 shown in FIG. 1A. In FIG. 5, the first and second sensing electrodes 310 and 320 and the first and second connection lines 330 and 340 are omitted for brevity. As described above, the flexible display apparatus 10 may include the touch screen panel 30 in which the shape deformation sensing units S31 and S32 are formed in the first and second connection lines 330 and 340.

An operating state of the flexible display apparatus 10 will be described with reference to FIG. 5.

The shape deformation sensing units S31 and S32 may be disposed on upper and lower sides and left and right sides of the flexible display apparatus 10, respectively. When the flexible display apparatus 10 is bent, at least one of the shape deformation sensing units S31 and S32 may be correspondingly bent.

As an example, when the flexible display apparatus 10 is bent based on a bending reference line L1, shape deformation sensing units S311 and S312, through which the bending reference line L1 passes, and shape deformation sensing units S31, which are disposed adjacent thereto, may be bent. Thus, electrical resistances of the shape deformation sensing units S311 and S312 through which the bending reference line L1 passes and the shape deformation sensing units S31 disposed adjacent thereto may vary accordingly. The bending of the flexible display apparatus 10 based on the bending reference line L1 may be measured by using the respective variations in electrical resistances.

As another example, when the flexible display apparatus 10 is bent based on a bending reference line L2, shape deformation sensing units S313 and S321, through which the bending reference line L2 passes, and shape deformation sensing units S31 and S32, which are disposed adjacent thereto, may be bent. Thus, electrical resistances of the shape deformation sensing units S313 and S321 through which the bending reference line L2 passes and shape deformation sensing unit S31 and S32 disposed adjacent thereto may vary accordingly. The bending of the flexible display apparatus 10 based on the bending reference line L2 may be measured by using the respective variations in electrical resistances.

Figure 6A:
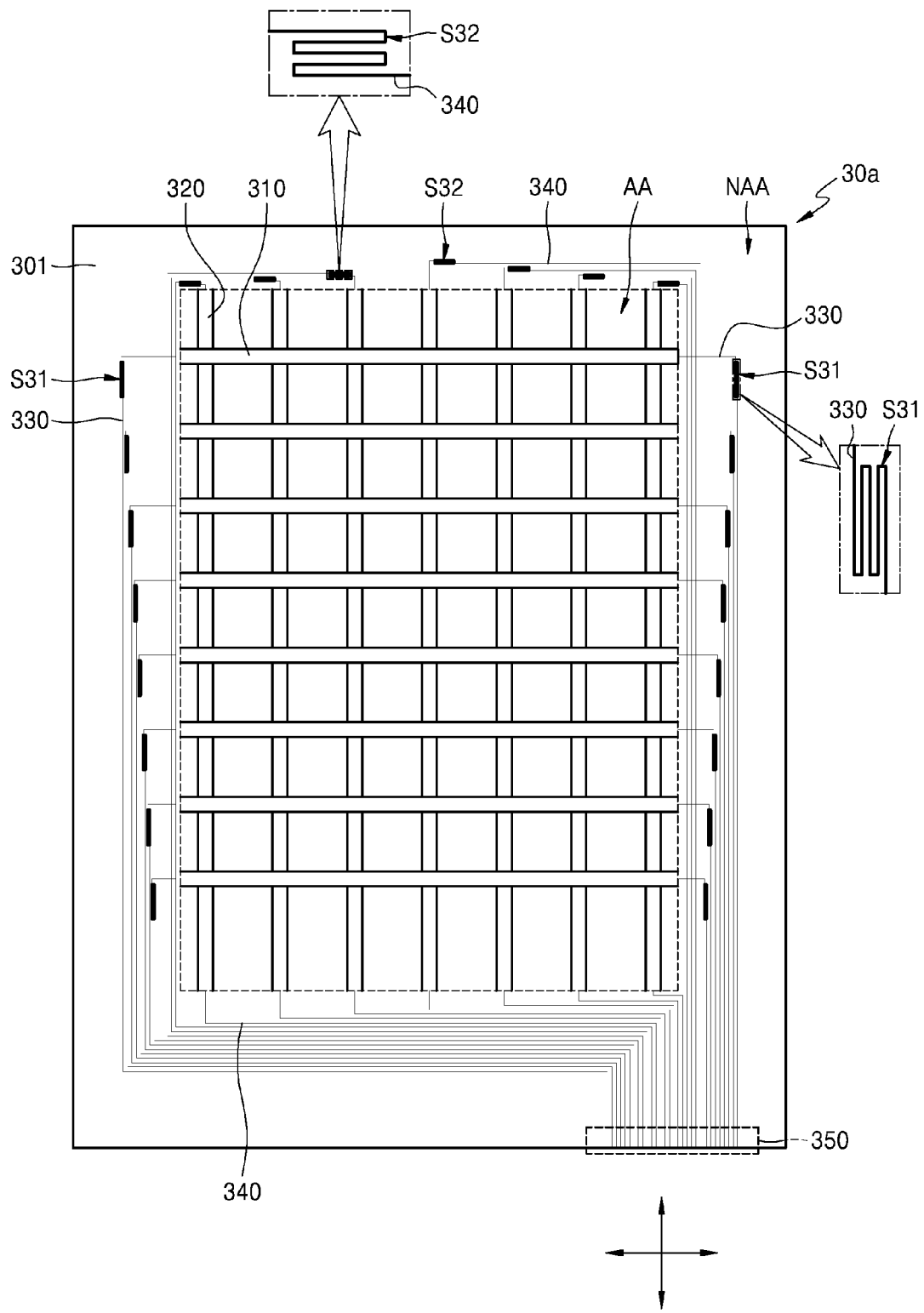
FIGS. 6A, 6B, 6C, and 6D are schematic plan views of modified examples of the touch screen panel of FIG. 1A.
Figure 6B:
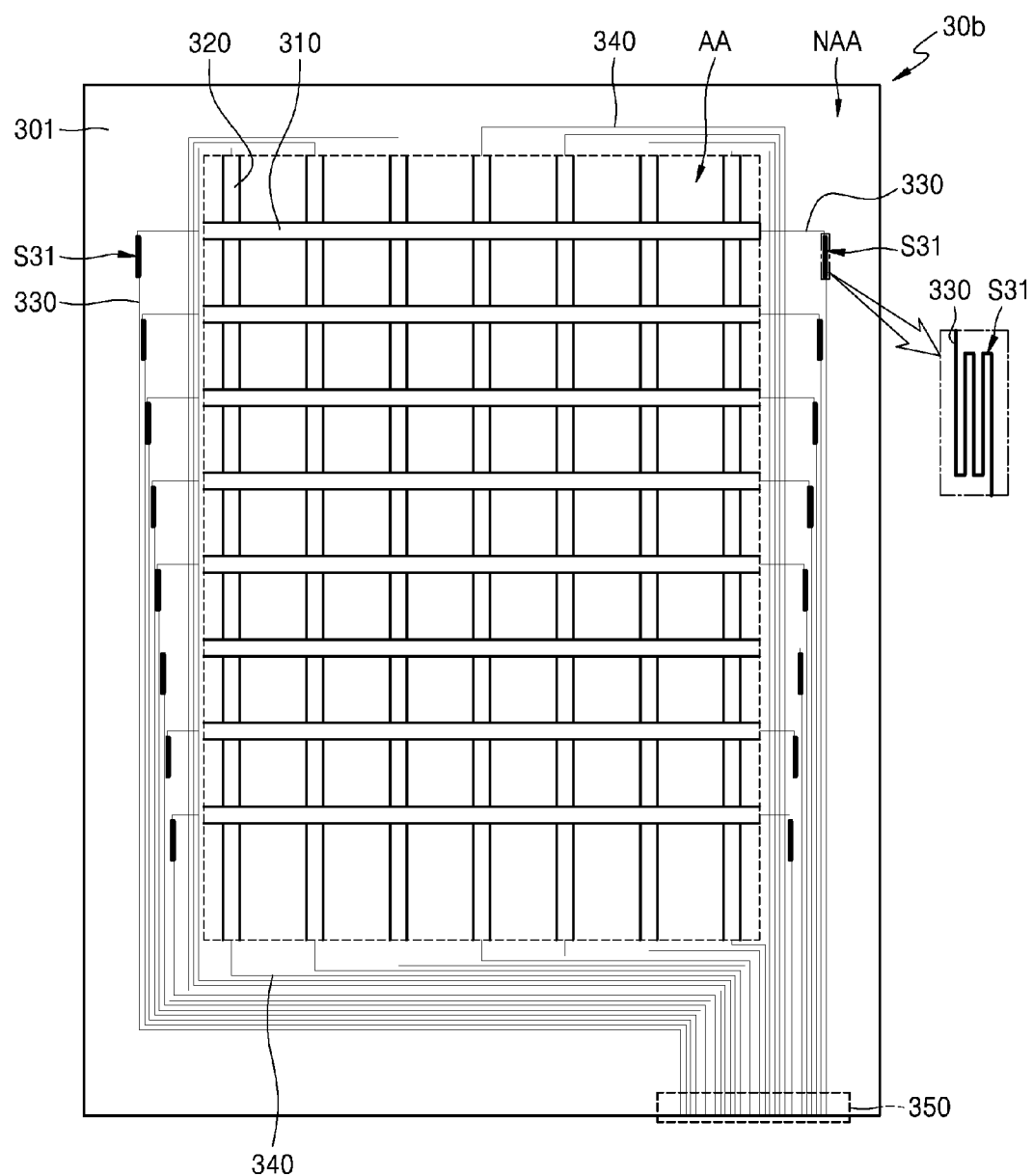
Figure 6C:
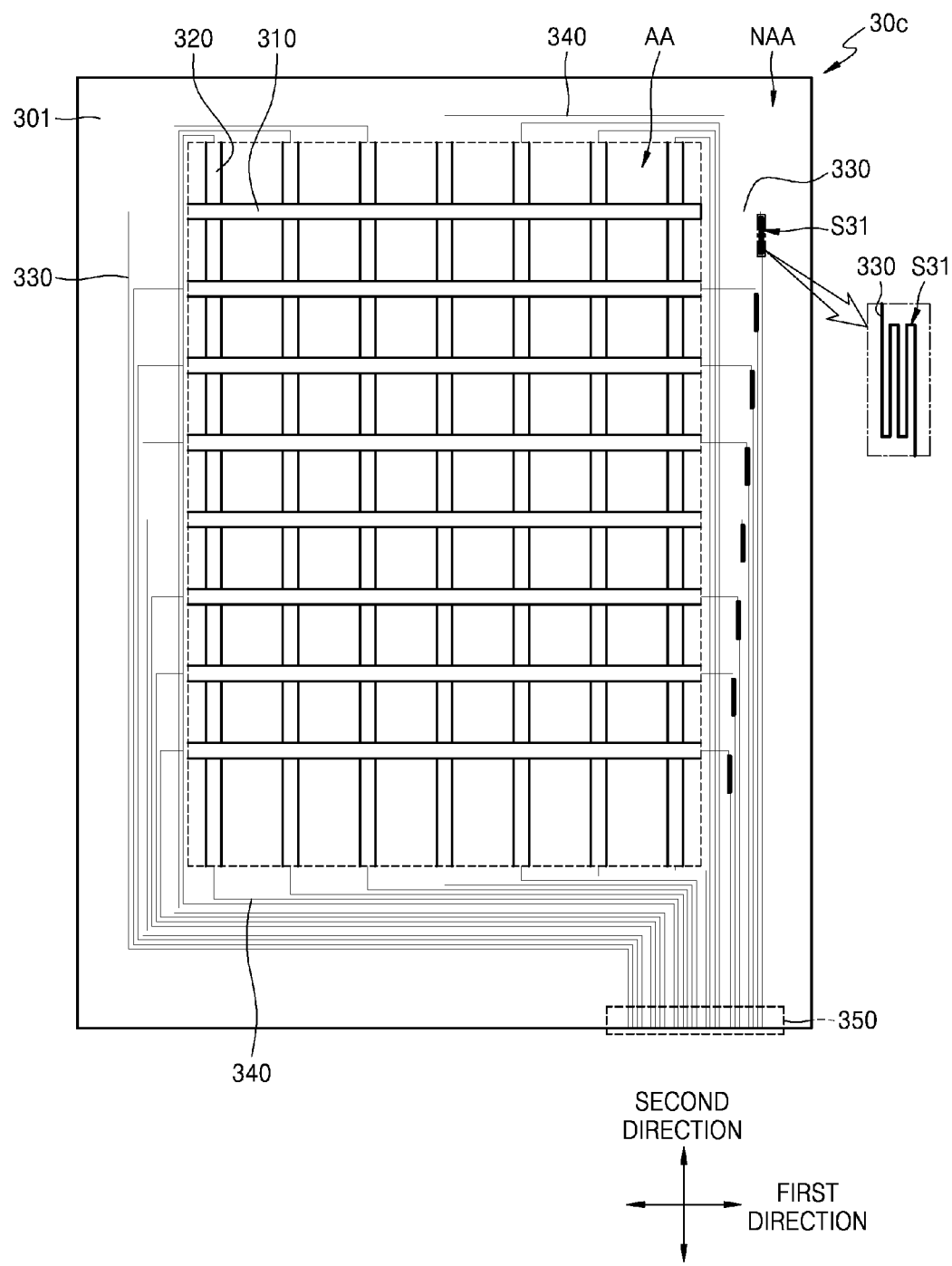
Figure 6D:
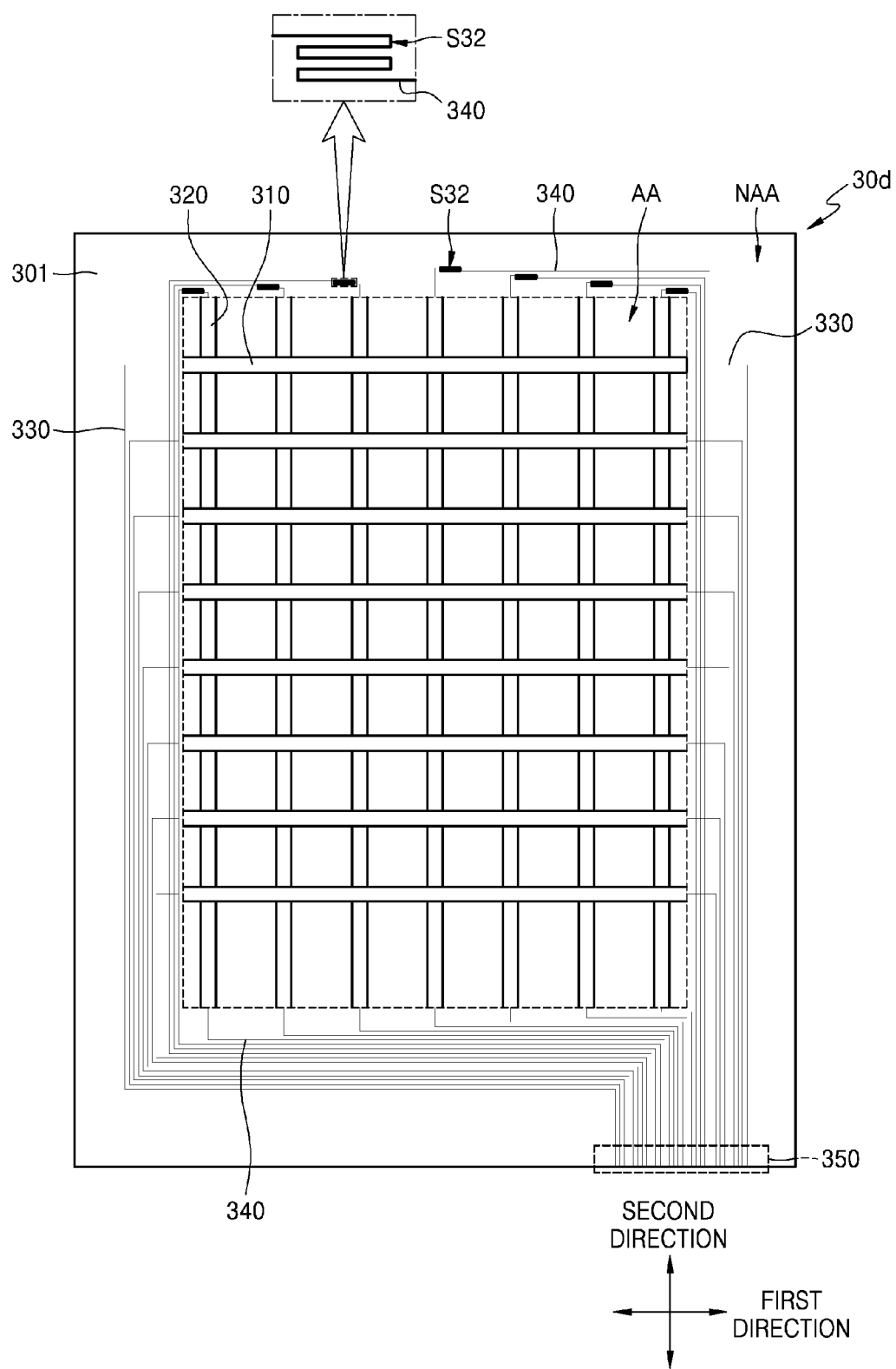

The above-described exemplary embodiment relates to an example in which respective components of the shape deformation sensing units S31 and S32 are formed on all four sides (upper, lower, left, and right sides) of the touch screen panel 30. However, positions where the shape deformation sensing units S31 and S32 are formed are not limited thereto, and may vary as needed or desired. For example, shape deformation sensing units, and/or components thereof, may be formed on three sides or less of the touch screen panel 30. The shape deformation sensing units may be formed on left, right, and upper sides of a touch screen panel 30a, as shown in FIG. 6A; formed on left and right sides of a touch screen panel 30b, as shown in FIG. 6B; formed on a right side of a touch screen panel 30c; as shown in FIG. 6C, or formed on an upper side of a touch screen panel 30d, as shown in FIG. 6D.

In addition, the above-described exemplary embodiment relates to an example in which respective components of the shape deformation sensing units S31 and S32 are formed on the touch screen panel 30. However, the shape deformation sensing units S21 and S22 and/or respective components thereof may be formed on another component of the flexible display apparatus 10. For example, the shape deformation sensing units S21 and S22 may be formed in the gate data lines 220 and 230 of the flexible display panel 20.

Figure 7:
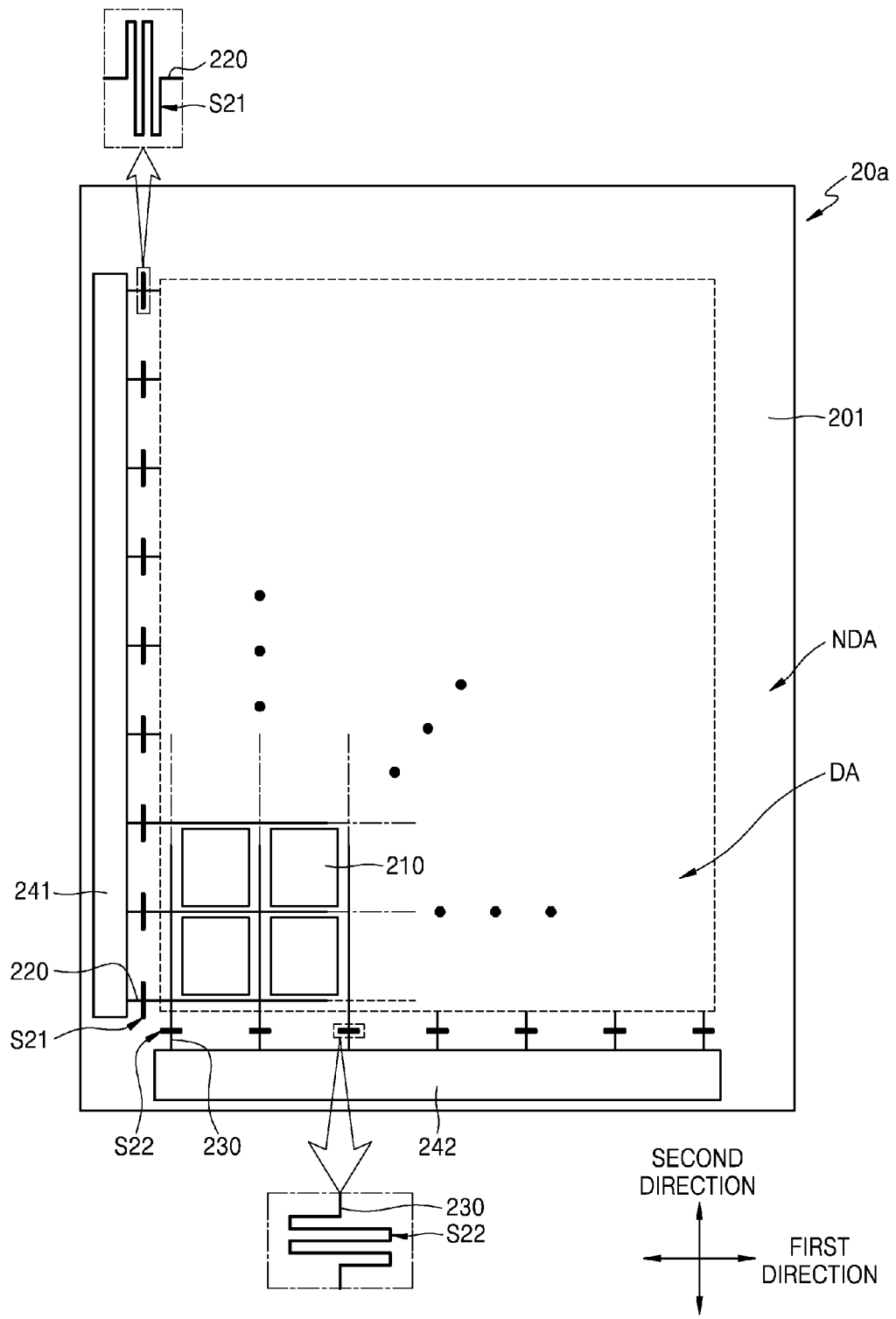
FIG. 7 is a plan view of a flexible display panel, according to another exemplary embodiment.

FIG. 7 is a plan view of a flexible display panel 20a according to another exemplary embodiment. Referring to FIG. 7, shape deformation sensing units S21 and S22 may be formed in connection lines 220 and 230 of the flexible display panel 20a, respectively.

The shape deformation sensing units S21 and S22 may be formed in at least one of the connection lines 220 and 230 of the flexible display panel 20a.

Each of the shape deformation sensing units S21 and S22 may include a strain gauge of which an electrical resistance varies based on a respective amount of shape deformation of the shape deformation sensing units S21 and S22. The electrical resistance of each of the shape deformation sensing units S21 and S22 may vary in proportion to the amount of strain applied during the shape deformation. For example, when the shape deformation sensing units S21 and S22 are being bent, lengths of electrical lines constituting the shape deformation sensing units S21 and S22 may increase, while sectional areas of the electrical lines may be reduced, thereby increasing electrical resistances of the shape deformation sensing units S21 and S22. By measuring the increased electrical resistances of the shape deformation sensing units S21 and S22, the bending of the flexible display apparatus 10 may be sensed and measured.

The shape deformation sensing units S21 may be formed by partially deforming patterns of the connection lines 220. For example, the shape deformation sensing unit S21 may extend from the connection lines 220. Each of the connection lines 220 may include an extension section that extends in the first direction. A repetitive pattern that reciprocates forward and backward in the second direction may be formed in the extension section of each of the shape deformation sensing units S21. The shape deformation sensing units S21 formed in the connection lines 220 may be disposed apart from one another in the second direction.

The shape deformation sensing units S22 may be formed by partially deforming patterns of the connection lines 230. For example, the shape deformation sensing units S22 may extend from the connection lines 230. Each of the connection lines 230 may include an extension section that extends in the second direction. A repetitive pattern that reciprocates forward and backward may be formed in the extension section of each of the shape deformation sensing units S22. The shape deformation sensing units S22 formed in the connection lines 230 may be disposed apart from one another in the first direction.

The exemplary embodiment shown in FIG. 7 has illustrated an example in which the shape deformation sensing units S22 are formed on left and lower sides of the flexible display panel 20a. However, positions where the shape deformation sensing units S21 and S22 are formed are not limited thereto, and may vary as needed or desired.

A flexible display apparatus according to one or more exemplary embodiments can sense a shape deformation by using circuit lines previously formed to operate the flexible display apparatus. Thus, the flexible display apparatus can prevent an increase in thickness and is able to precisely sense a shape deformation.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

In the specification, and particularly, in the claims, the singular forms "a", "an", and "the" are intended to include the plural forms as well, unless the context clearly indicates otherwise. Also, when a "range" is described herein, individual values that fall within the range are applied, unless the context clearly indicates otherwise, and it will be understood that the individual values that fall within the range are described in the specification. Unless explicitly defined in a specific order herein, respective steps described herein may be performed in any of various ways. In particular, the respective steps may be performed in a specified order, substantially at the same time, or in reverse order. It will be understood that all examples or exemplary terms (e.g., etc.) may be used herein to describe exemplary embodiments, the exemplary embodiments should not be limited by these examples or exemplary terms, without departing from the spirit and scope of the present disclosure as defined by the claims.

What is claimed is:

1. A flexible display apparatus comprising:
   a flexible display panel which includes a display area in which a plurality of pixels are disposed, and a non-display area formed outside of the display area and in which a first plurality of connection lines connected to the pixels are disposed, wherein at least a portion of the flexible display panel is capable of being bent; and
   a touch screen panel which includes an active area in which sensing electrodes are disposed, and a non-active area formed outside of the active area and in which a second plurality of connection lines connected to the sensing electrodes are disposed, wherein a shape deformation sensor is formed in at least one from among the first plurality of connection lines of the non-display area and the second plurality of connection lines of the non-active area, wherein the shape deformation sensor is configured to sense a shape deformation of the flexible display panel.

2. The flexible display apparatus of claim 1, wherein the shape deformation sensor includes a strain gauge of which an electrical resistance varies based on a sensed amount of the shape deformation.

3. The flexible display apparatus of claim 2, wherein the shape deformation sensor includes a same material as the at least one of the first plurality of connection lines of the flexible display panel and the second plurality of connection lines of the touch screen panel in which the shape deformation sensor is formed.

4. The flexible display apparatus of claim 2, wherein the shape deformation sensor extends from the at least one of the first plurality of connection lines of the flexible display panel and the second plurality of connection lines of the touch screen panel in which the shape deformation sensor is formed.

5. The flexible display apparatus of claim 2, wherein the sensing electrodes of the touch screen panel comprise first sensing electrodes formed in a first direction and second sensing electrodes formed in a second direction that intersects the first direction, and the second plurality of connection lines of the touch screen panel comprises first connection lines connected to both end portions of the first sensing electrodes and second connection lines connected to both end portions of the second sensing electrodes.

6. The flexible display apparatus of claim 5, wherein at least two sections of the first connection lines extend in the second direction, and a respective sensor component of the shape deformation sensor is formed in each of the at least two sections of the first connection lines that extend in the second direction.

7. The flexible display apparatus of claim 6, wherein the respective components of the shape deformation sensor formed in the first connection lines are disposed apart from one another in the second direction.

8. The flexible display apparatus of claim 5, wherein at least two sections of the second connection lines extend in the first direction, and a respective component of the shape deformation sensor is formed in each of the sections of the at least two second connection lines that extend in the first direction.

9. The flexible display apparatus of claim 8, wherein the respective components of the shape deformation sensor formed in the second connection lines are disposed apart from one another in the first direction.

10. A method for sensing a deformation in a flexible display apparatus, the flexible display apparatus comprising:

a flexible display panel which includes a display area in which a plurality of pixels are disposed, and a non-display area formed outside of the display area and in which a first plurality of connection lines connected to the pixels are disposed, wherein at least a portion of the flexible display panel is capable of being bent; and a touch screen panel which includes an active area in which sensing electrodes are disposed, and a non-active area formed outside of the active area and in which a second plurality of connection lines connected to the sensing electrodes are disposed, and the method comprising:

arranging a shape deformation sensor in at least one from among the first plurality of connection lines of the non-display area and the second plurality of connection lines of the non-active area; and sensing, by the shape deformation sensor, a shape deformation of the flexible display panel.

11. The method of claim 10, wherein the sensing comprises sensing an amount of shape deformation and determining a type of shape deformation, wherein the type of shape deformation includes at least one from among a folding deformation and a bending deformation.

12. The method of claim 11, wherein when the type of shape deformation is determined as a folding deformation, the sensing further comprises determining a folding direction with respect to the flexible display apparatus.

13. The method of claim 11, wherein when the type of shape deformation is determined as a bending deformation, the sensing further comprises determining a bending direction which includes at least one from among a concave direction and a convex direction with respect to a display surface of the flexible display apparatus.

14. The method of claim 10, wherein the arranging includes providing a strain gauge in the shape deformation sensor, and wherein the sensing includes measuring, by the strain gauge, an electrical resistance.

15. The method of claim 10, wherein the arranging includes providing a respective component of the shape deformation sensor in each of the first plurality of connection lines of the flexible display panel and in each of the second plurality of connection lines of the touch screen panel.

* * * * *